US012749559B2

(12) United States Patent
Williams

(10) Patent No.: US 12,749,559 B2
(45) Date of Patent: Sep. 29, 2026

(54) SYSTEM AND METHOD FOR FACILITATING CLINICAL TRIAL ENROLLMENT

(71) Applicant: Chadwick Ian Williams, Middle Sackville (CA)

(72) Inventor: Chadwick Ian Williams, Middle Sackville (CA)

( * ) Notice: Subject to any disclaimer, the term of this patent is extended or adjusted under 35 U.S.C. 154(b) by 5 days.

(21) Appl. No.: 18/840,648

(22) PCT Filed: Nov. 29, 2022

(86) PCT No.: PCT/CA2022/000058
§ 371 (c)(1),
(2) Date: Aug. 22, 2024

(87) PCT Pub. No.: WO2023/159294
PCT Pub. Date: Aug. 31, 2023

(65) Prior Publication Data

US 2025/0174316 A1 May 29, 2025

(30) Foreign Application Priority Data

Feb. 22, 2022 (CA) ................................ CA 3150412

(51) Int. Cl.
*G16H 10/20* (2018.01)
*G06F 3/0482* (2013.01)
(Continued)

(52) U.S. Cl.
CPC ........... *G16H 10/20* (2018.01); *G06F 3/0482* (2013.01); *G06F 16/9558* (2019.01); *G16H 10/60* (2018.01)

(58) Field of Classification Search
CPC ........ G16H 10/20; G16H 10/60; G16H 40/20; G06F 3/0482; G06F 16/9558
See application file for complete search history.

(56) References Cited

U.S. PATENT DOCUMENTS 11,842,802 B2 * 12/2023 Mao ........................ G16H 10/20
2002/0099570 A1 * 7/2002 Knight ................... G16H 10/20 705/2

(Continued)

OTHER PUBLICATIONS

Oh YJ, Zhang J, Fang ML, Fukuoka Y. A systematic review of artificial intelligence chatbots for promoting physical activity, healthy diet, and weight loss. Int J Behav Nutr Phys Act. Dec. 11, 2021;18(1):160. doi: 10.1186/s12966-021-01224-6. PMID: 34895247; PMCID: PMC8665320. (Year: 2021).*

(Continued)

*Primary Examiner* — Sun M Li
(74) *Attorney, Agent, or Firm* — Thompson Hine LLP

(57) ABSTRACT

A system and method for facilitating clinical trial enrollment. A clinical trial information database is provided. The clinical trial information database has stored therein clinical trial information of at least a clinical trial with the clinical trial information being indicative of clinical trial criteria of the at least a clinical trial and contact information of the at least a clinical trial's coordinator. A server computer is connected to the Internet and the clinical trial database. The server computer executes computer-executable instructions stored in a non-transient memory thereof and performs generates data indicative of an interactive Internet website for facilitating clinical trial enrollment. The interactive Internet website enables communication between the server computer and users of client computers connected to the Internet. A request for clinical trial information is received from a user via the Internet website executed on the user's client computer. The user is prompted and enabled to provide information indicative of patient characteristics. The received patient characteristics are compared with the clinical trial criteria retrieved from the clinical trial information database and information indicative of the patient's eligi- (Continued)

bility or ineligibility to a trial is provided to the user's client computer.

17 Claims, 7 Drawing Sheets

(51) Int. Cl.
*G06F 16/955* (2019.01)
*G16H 10/60* (2018.01)

(56) References Cited

U.S. PATENT DOCUMENTS

| | | | | |
|---|---|---|---|---|
| 2003/0108938 | A1* | 6/2003 | Pickar | G16H 70/40 702/20 |
| 2004/0078216 | A1 | 4/2004 | Toto | |
| 2007/0214012 | A1* | 9/2007 | Loew | G16H 10/60 600/300 |
| 2008/0133270 | A1 | 6/2008 | Michelson et al. | |
| 2014/0316793 | A1* | 10/2014 | Pruit | G16H 10/20 705/2 |
| 2015/0161336 | A1* | 6/2015 | Kalathil | G16H 70/20 705/3 |
| 2018/0046780 | A1* | 2/2018 | Graiver | G06F 40/44 |
| 2019/0244683 | A1* | 8/2019 | Francois | G16H 10/60 |
| 2020/0005906 | A1* | 1/2020 | Wang | G16H 10/20 |
| 2020/0357490 | A1* | 11/2020 | Kartoun | G16H 10/20 |
| 2020/0381087 | A1* | 12/2020 | Ozeran | G06F 16/31 |
| 2022/0068443 | A1* | 3/2022 | Ransom | G16H 10/20 |
| 2022/0215908 | A1* | 7/2022 | Padmos | G16H 10/60 |
| 2022/0336061 | A1 | 10/2022 | Mackenzie et al. | |

OTHER PUBLICATIONS

Köpcke F, Prokosch Hu. Employing computers for the recruitment into clinical trials: a comprehensive systematic review. J Med Internet Res. Jul. 1, 2014;16(7):e161. doi: 10.2196/jmir.3446. PMID: 24985568; PMCID: PMC4128959. (Year: 2014).*

Köpcke F, Trinczek B, Majeed RW, Schreiweis B, Wenk J, Leusch T, Ganslandt T, Ohmann C, Bergh B, Röhrig R, Dugas M, Prokosch HU. Evaluation of data completeness in the electronic health record for the purpose of patient recruitment into clinical trials: a retrospective analysis of element presence. (Year: 2013).*

V. Andronikou, E. Karanastasis, E. Chondrogiannis, K. Tserpes and T. Varvarigou, "Semantically-enabled Intelligent Patient Recruitment in Clinical Trials," 2010 International Conference on P2P, Parallel, Grid, Cloud and Internet Computing, Fukuoka, Japan, 2010,pp. 326-331, doi: 10.1109/3PGCIC.2010.54. (Year: 2010).*

Canadian Intellectual Property Office, International Search Report and Written Opinion, issued Apr. 4, 2023, which pertains to PCT Application No. PCT/CA2022/000058. 15 pgs.

Fang et al., Combining human and machine intelligence for clinical trial eligibility querying. Journal of the American Medical Informatics Association, 29:7, 2022. pp. 1161-1171.

Bardach et al., Assessment of automated clinical trial recruitment and enrolment using patient-facing technology. BMJ Health & Care Informatics, 28:1, 2021. 5 pgs.

Correa et al., AGUIA: autonomous graphical user interface assembly for clinical trials semantic data services. BMC Medical Informatics and Decision Making, 10:65, 2010. pp. 1-13.

Rosenbaum et al., Easily configured real-time CPOE Pick Off Tool supporting focused clinical research and quality improvement. Journal of the American Medical Informatics Association, 21:3, 2014. pp. 564-568.

* cited by examiner

SYSTEM AND METHOD FOR FACILITATING CLINICAL TRIAL ENROLLMENT

This application is a national stage filing of International Application No. PCT/CA2022/000058 filed on Nov. 29, 2022 (corresponding to International Publication No. WO 2023/159294), which in turn claims priority to Canadian Patent Application 3150412 filed on Feb. 22, 2022. The entire contents of both of these applications are hereby incorporated by reference.

FIELD

The present disclosure relates to medical information technology, and more particularly to a system and method for facilitating clinical trial enrollment.

BACKGROUND

A clinical trial is a medical research sturdy involving human subjects to determine if a new medical drug, medical device, or medical procedure is safe and effective for human use. Clinical trials are scheduled after successful pre-clinical testing.

Because clinical trials involve experimental drugs, devices, or procedures, a host of safeguards has been set in place to protect the human subject as much as possible. In particular, standards and guidelines are in place to protect the confidentiality and rights of human trial subjects.

Due to these mandated safeguards and due to increasing complexity of the clinical trials, the average number of eligibility criteria used to screen volunteers has risen exponentially over the years, resulting in a more and more complex enrollment process and a reduced number of individuals that are eligible for a clinical trial.

Currently, a physician is required to actively contact various pharmaceutical groups to see if they have clinical trial options and then the physician, nurse, or researcher coordinator would need to manually go through the clinical trial criteria to see if the patient is eligible. This is a cumbersome and time consuming process and results in many patients never being offered access to clinical trials.

It may be desirable to provide a system and method for facilitating clinical trial enrollment.

It also may be desirable to provide a system and method for facilitating clinical trial enrollment that enables a physician to easily access clinical trials a patient is eligible to participate.

It also may be desirable to provide a system and method for facilitating clinical trial enrollment that makes it easy and time efficient to identify patients for clinical trials.

It also may be desirable to provide a system and method for facilitating clinical trial enrollment that maintains patient confidentiality.

SUMMARY

Accordingly, one advantage of the present disclosure is to provide a system and method for facilitating clinical trial enrollment.

Another advantage of the present disclosure is to provide a system and method for facilitating clinical trial enrollment that enables a physician to easily access clinical trials a patient is eligible to participate.

Another advantage of the present disclosure is to provide a system and method for facilitating clinical trial enrollment that makes it easy and time efficient to identify patients for clinical trials.

Another advantage of the present disclosure is to provide a system and method for facilitating clinical trial enrollment that maintains patient confidentiality.

According to one aspect, there is provided a method for facilitating clinical trial enrollment. A clinical trial information database is provided. The clinical trial information database has stored therein clinical trial information of at least a clinical trial with the clinical trial information being indicative of clinical trial criteria of at least a clinical trial and contact information of the at least a clinical trial's coordinator. A server computer is connected to the Internet and the clinical trial database. The server computer executes computer-executable instructions stored in a non-transient memory thereof and generates data indicative of an interactive Internet website for facilitating clinical trial enrollment. The interactive Internet website enables communication between the server computer and users of client computers connected to the Internet. A request for clinical trial information is received from a user via the Internet website executed on the user's client computer. The user is prompted and enabled to provide information indicative of patient characteristics. The received patient characteristics are compared with the clinical trial criteria retrieved from the clinical trial information database and information indicative of the patient's eligibility or ineligibility to a trial is provided to the user's client computer.

According to one aspect, there is provided a method for facilitating clinical trial enrollment. A clinical trial information database is provided. The clinical trial information database has stored therein clinical trial information of at least a clinical trial with the clinical trial information being indicative of clinical trial criteria of the at least a clinical trial and contact information of the at least a clinical trial's coordinator. A server computer is connected to the Internet and the clinical trial database. The server computer executes computer-executable instructions stored in a non-transient memory thereof and performs generates data indicative of an interactive Internet website for facilitating clinical trial enrollment. The interactive Internet website enables communication between the server computer and users of client computers connected to the Internet. A request for clinical trial information is received from a user via the Internet website executed on the user's client computer. The user is prompted and enabled to provide information indicative of patient characteristics. The received patient characteristics are compared with the clinical trial criteria retrieved from the clinical trial information database and information indicative of the patient's eligibility or ineligibility to a trial is provided to the user's client computer. If the information indicative of the patient's eligibility or ineligibility to a trial is indicative of the patient being eligible to a clinical trial, the server computer retrieves the contact information of the clinical trial's coordinator from the clinical trial information database and provides the contact information to the user's client computer.

According to one aspect, there is provided a method for facilitating clinical trial enrollment. A clinical trial information database is provided. The clinical trial information database has stored therein clinical trial information of at least a clinical trial with the clinical trial information being indicative of clinical trial criteria of the at least a clinical trial and contact information of the at least a clinical trial's coordinator. A server computer is connected to the Internet and the clinical trial database. The server computer executes computer-executable instructions stored in a non-transient memory thereof and performs generates data indicative of an interactive Internet website for facilitating clinical trial enrollment. The interactive Internet website enables communication between the server computer and users of client computers connected to the Internet. A request for clinical trial information is received from a user via the Internet website executed on the user's client computer. The user is prompted and enabled to provide information indicative of patient characteristics. The received patient characteristics are compared with the clinical trial criteria retrieved from the clinical trial information database and information indicative of the patient's eligibility or ineligibility to a trial is provided to the user's client computer. The server computer receives clinical trial information of a clinical trial with the clinical trial information being indicative of clinical trial criteria of the clinical trial and contact information of the clinical trial's coordinator and stores the clinical trial information in the clinical trial information database.

According to one aspect, there is provided a system for facilitating clinical trial enrollment. A clinical trial information database has stored therein clinical trial information of at least a clinical trial with the clinical trial information being indicative of clinical trial criteria of the at least a clinical trial and contact information of the at least a clinical trial's coordinator. A server computer is connected to the Internet and the clinical trial database. The server computer when executing computer-executable instructions stored in a non-transient memory thereof performs generating data indicative of an interactive Internet website for facilitating clinical trial enrollment, the interactive Internet website enabling communication between the server computer and users of client computers connected to the Internet. A request for clinical trial information is received from a user via the Internet website executed on the user's client computer. The user is prompted and enabled to provide information indicative of patient characteristics. The received patient characteristics are compared with the clinical trial criteria retrieved from the clinical trial information database and information indicative of the patient's eligibility or ineligibility to a trial is provided to the user's client computer.

An advantage of the present disclosure is that it provides a system and method for facilitating clinical trial enrollment.

A further advantage of the present disclosure is that it provides a system and method for facilitating clinical trial enrollment that enables a physician to easily access clinical trials a patient is eligible to participate.

A further advantage of the present disclosure is that it provides a system and method for facilitating clinical trial enrollment that makes it easy and time efficient to identify patients for clinical trials.

A further advantage of the present disclosure is that it provides a system and method for facilitating clinical trial enrollment that maintains patient confidentiality.

BRIEF DESCRIPTION OF THE DRAWINGS

An embodiment is described below with reference to the accompanying drawings, in which.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, certain methods and materials are now described.

Figure 1:
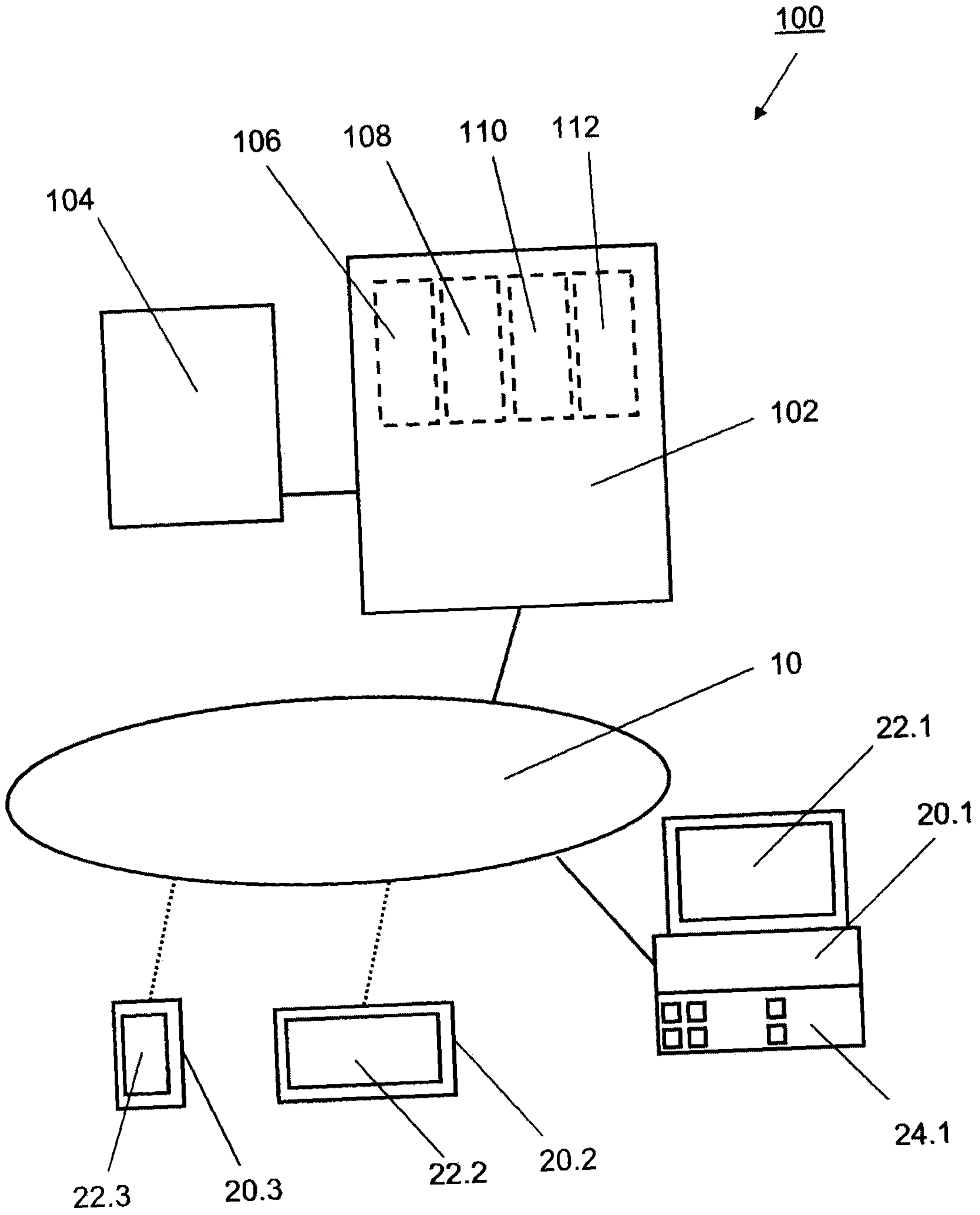
FIG. 1 is a simplified block diagram illustrating a system for facilitating clinical trial enrollment according to an embodiment.
Figure 2:
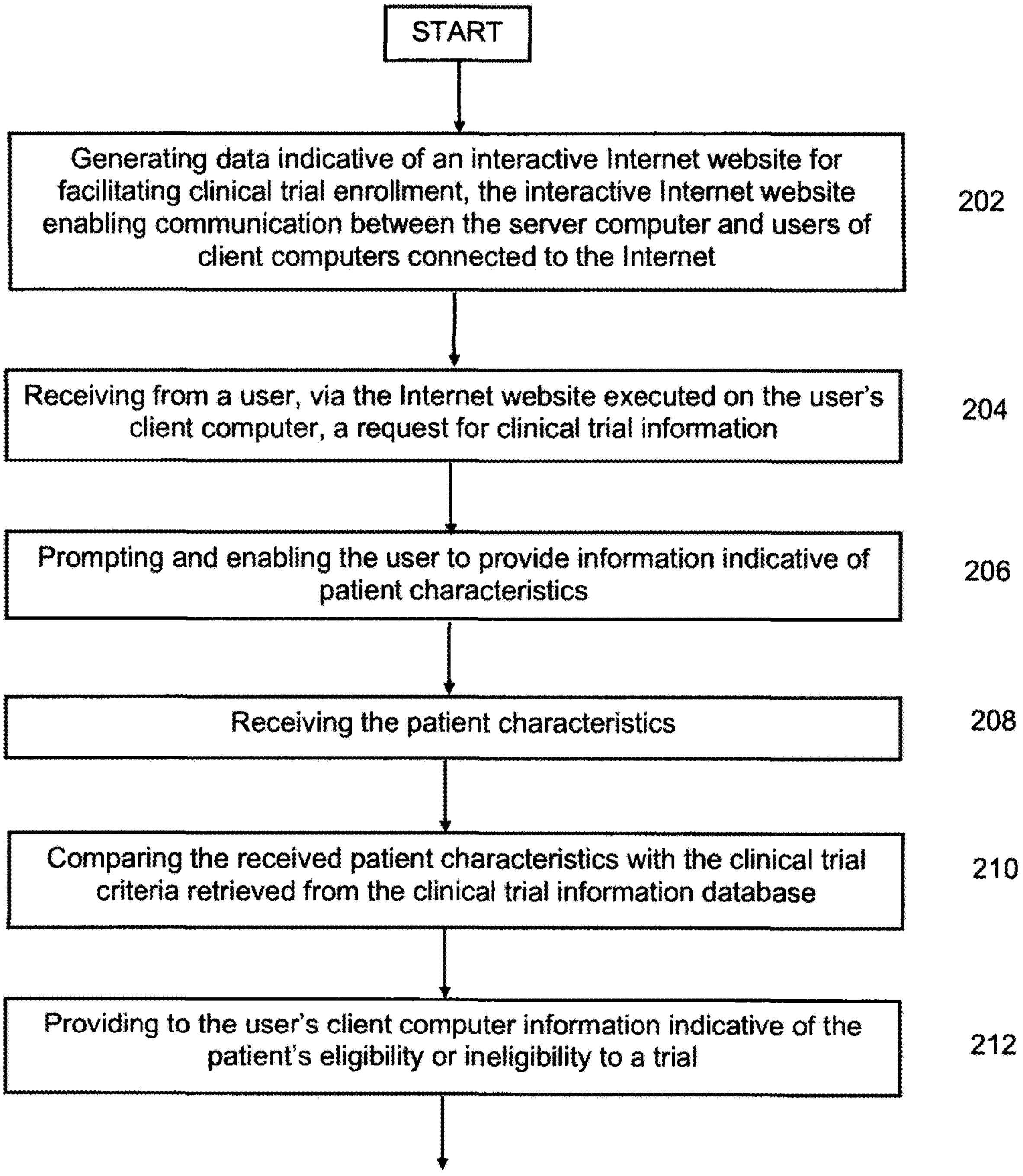
FIG. 2 is a simplified flow diagram illustrating a method for facilitating clinical trial enrollment according to an embodiment.
Figure 2:
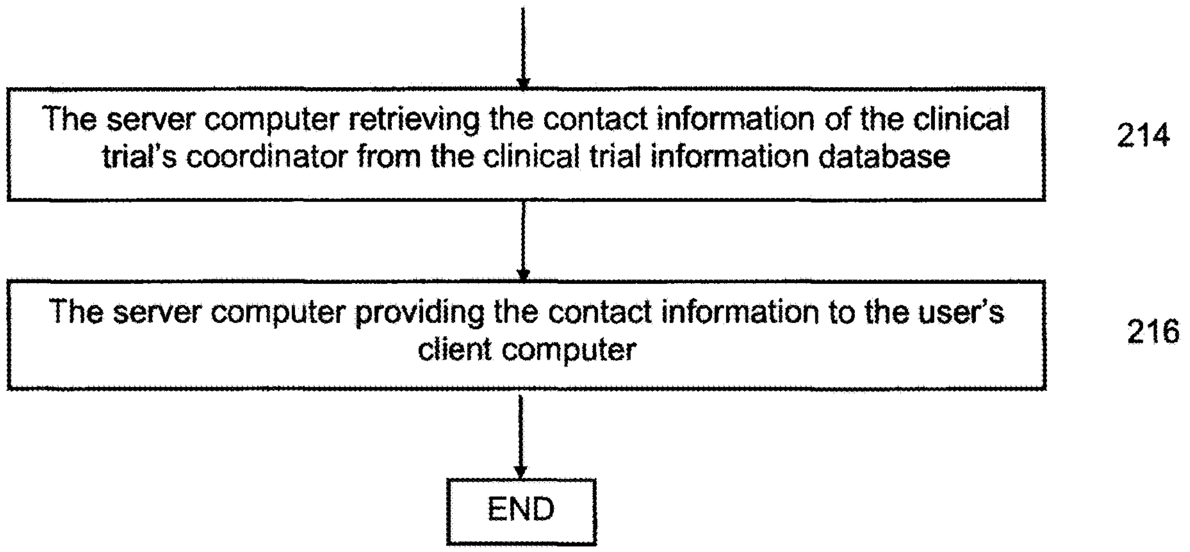

Referring to FIG. 1 a system 100 for facilitating clinical trial enrollment according to an embodiment is provided. The system 100 comprises a server computer 102 connected to the Internet 10 and a clinical trial information database 104 connected to the server computer 102. The clinical trial information database 104 has stored therein clinical trial information of at least a clinical trial with the clinical trial information being indicative of clinical trial criteria of the at least a clinical trial and contact information of the at least a clinical trial's coordinator. The clinical trial information database 104 can be updated, for example, in predetermined time intervals or upon request by a clinical trial provider. The updating may be performed by a system administrator, by a clinical trial provider, for example, through the interactive Internet website, by the server computer accessing a clinical trial providers database using, for example, hyperlink technology, or a combination thereof. The server computer 102 when executing computer-executable instructions stored in a non-transient memory thereof such as, for example, a hard drive, performs the task of an Internet based method for facilitating clinical trial enrollment, certain embodiments of which will be described hereinbelow, with the main tasks comprising: generating and operating an interactive Internet website; managing receipt of the clinical trial information and storage of the same in the clinical trial information database 104; enabling communication between the server computer 102 and users of client computers 20.1, 20.2, 20.3 connected to the Internet 10; prompting and enabling the user to provide information indicative of patient characteristics; querying the clinical trial information database 104; and, comparing the received patient characteristics with clinical trial criteria retrieved from the clinical trial information database 104 and providing to the user's client computer information indicative of the patient's eligibility to a trial.

The clinical trial information database 104 is, in one case, generated and operated using a standard SQL based database management system such as, for example, MySQL, PostGreSQL, Oracle, or Sybase. The server computer 102 is, in one case, a standard server computer capable of executing a web server application such as, for example, the widely used web server software "Apache HTTP Server." Optionally, the server computer 102 comprises multiple processing modules with each processing module being associated with the processing of a specific task such as, for example, database management module 106, Internet communication module 108, comparison module 110, and account management module 112. The multiple processing modules may be implemented software based—multiple software platforms—or hardware based—multiple processors.

The interactive Internet website is, in one case, created as a dynamic website employing widely used software systems such as, for example, Common Gateway Interface (CGI), Java Servlets, or Jakarta Server Pages. The webpages of the interactive Internet website are provided based on widely used Graphical User Interface (GUI) technology enabling the user to interact, for example, by clicking on selected icons, selecting from drop-down menus, and enter text into text fields. In one case, the interactive Internet website is adapted to enable communication with users of various different types of client computers having Internet 10 connectivity such as, for example, desktop and laptop computers 20.1 having monitor 22.1 and keyboard 24.1, tablet computers 20.2 having touchscreen 22.2, and smartphones 20.3 having touchscreen 22.3. The interactive Internet website may be implemented for mobile devices such as, for example, tablet computers and smartphones using Mobile App technology.

Figure 3:
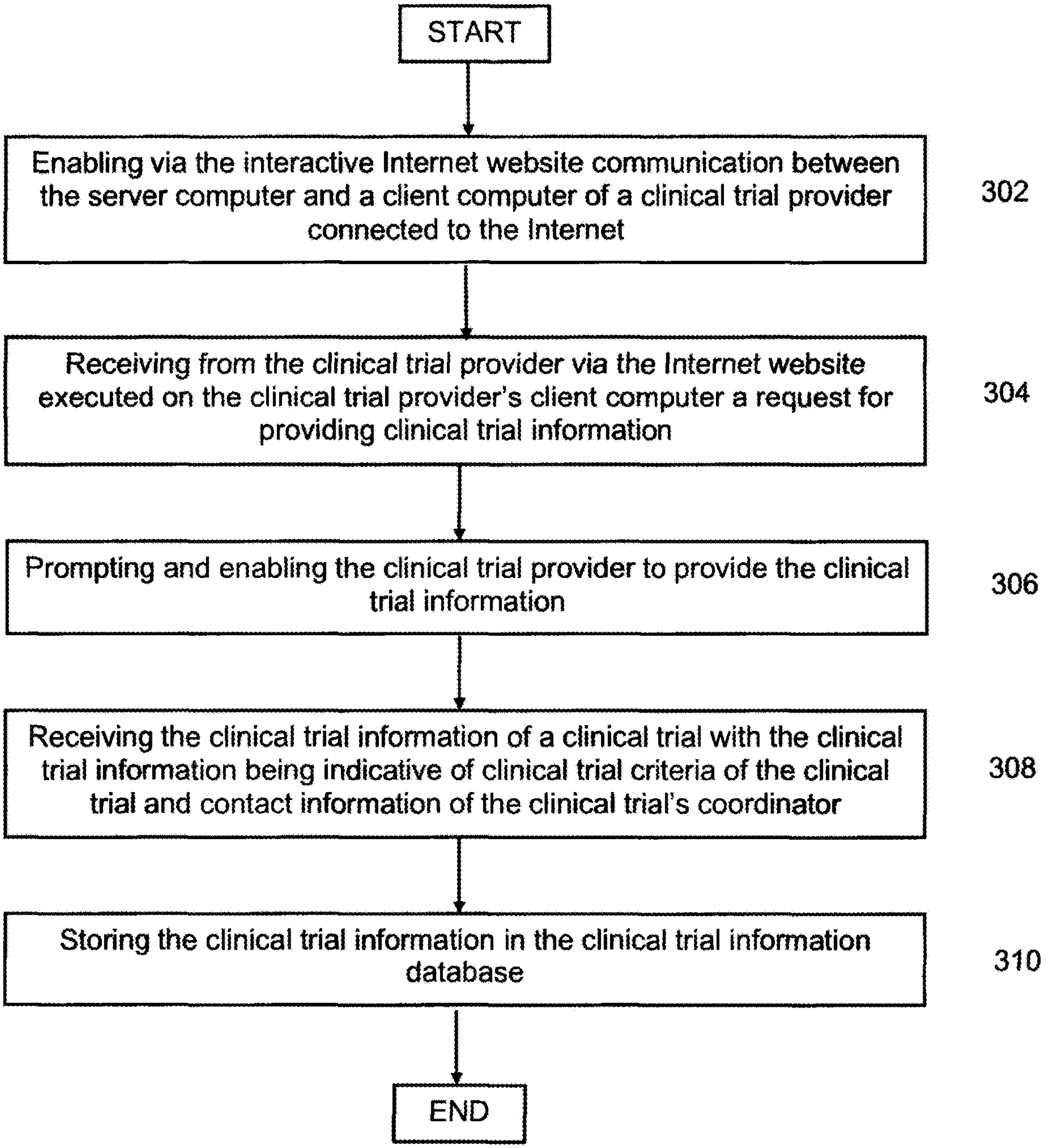
FIG. 3 is a simplified flow diagram illustrating a method for facilitating clinical trial enrollment according to an embodiment.
Figure 4:
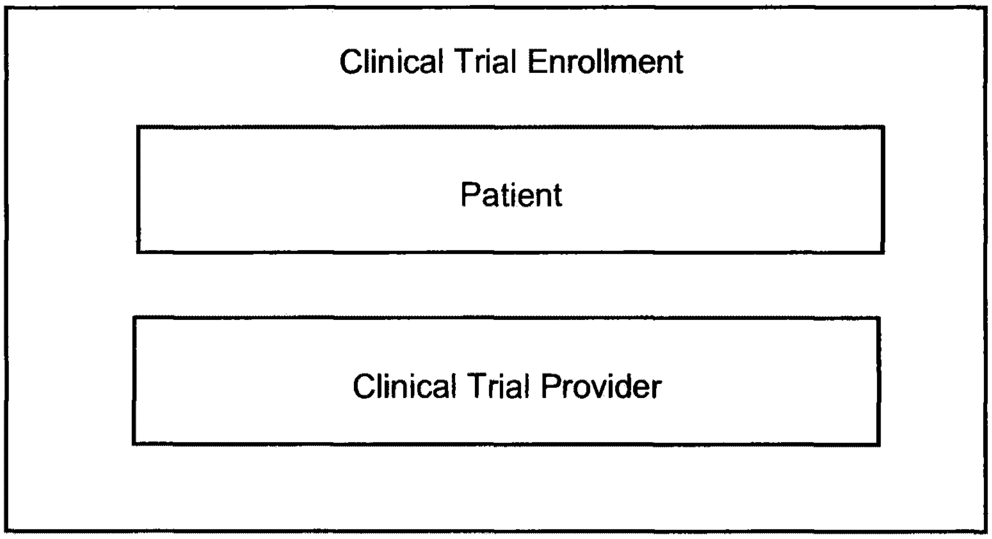
FIG. 4 is a simplified block diagram illustrating a webpage for providing patient characteristics of the method for facilitating clinical trial enrollment according to an embodiment.
Figure 5:
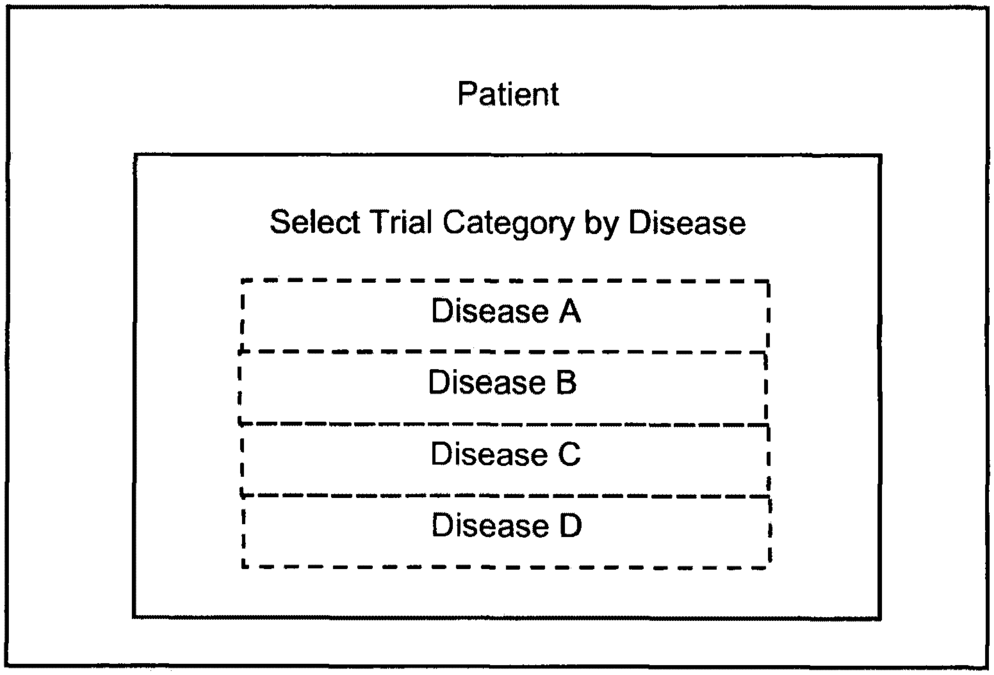
FIG. 5 is a simplified block diagram illustrating a webpage for providing patient characteristics of the method for facilitating clinical trial enrollment according to an embodiment.
Figure 6:
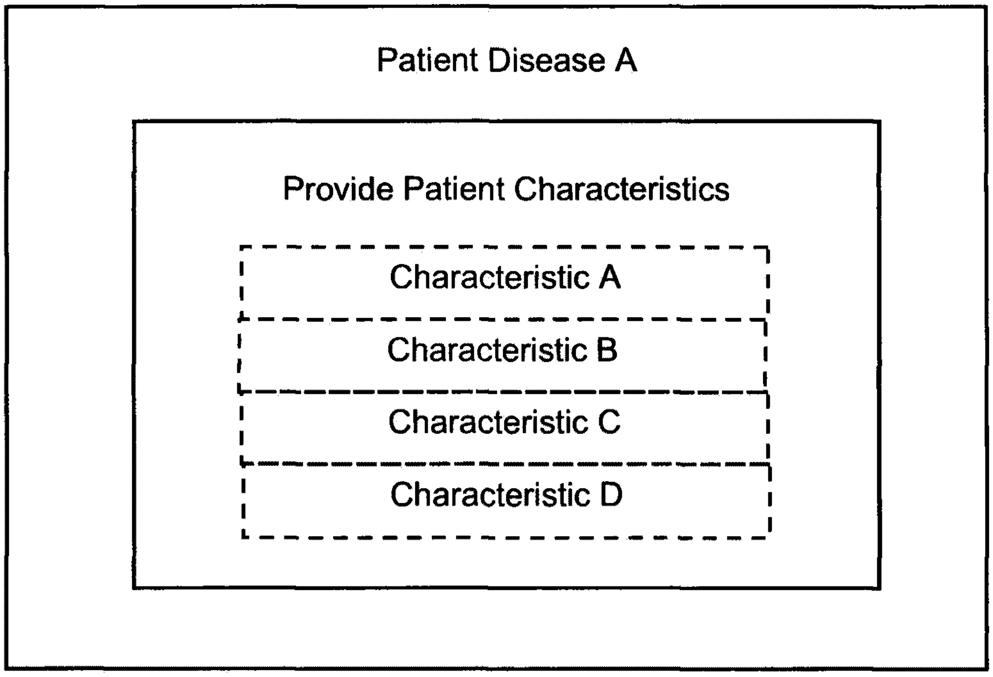
FIG. 6 is a simplified block diagram illustrating a webpage for providing patient characteristics of the method for facilitating clinical trial enrollment according to an embodiment.

Referring to FIGS. 2 to 8 an Internet based method for facilitating clinical trial enrollment according to an embodiment is provided. The server computer 102 generates—202—data indicative of an interactive Internet website for facilitating clinical trial enrollment. The interactive Internet website enables communication between the server computer 102 and users of client computers 20.1, 20.2, 20.3 connected to the Internet 10. The user typically being a medical practitioner such as, for example, a physician or nurse, is presented with a homepage, an example, of which is illustrated in FIG. 4, enabling to select "Patient" for information about the availability of a clinical trial for the medical practitioner's patient, by clicking on the respective button which generates a request for clinical trial information—204—at the server computer 102. The user is then prompted and enabled to provide information indicative of patient characteristics—206. For example, the user is first presented with a webpage, as illustrated in FIG. 5, enabling to select a disease for which it is desired to find a clinical trial by using a drop-down menu and clicking on the respective disease such as, for example, disease B "Inflammatory Bowel Disease." Upon selection of the disease, the user is presented with a second webpage, as illustrated in FIG. 6, enabling to provide patient characteristics by using a drop-down menu and clicking on the respective characteristics such as, for example, "male/female/other," "age ranges," "Crohn's disease or ulcerative colitis," "disease clinical severity," "endoscopic severity," "previous medical therapies," "current medical therapies," "previous surgeries," "extra-intestinal manifestations of inflammatory bowel disease," "racial background," "disease extent," "disease location," "disease behavior," etc. Upon receipt of the patient characteristics—208—the same are compared with the clinical trial criteria retrieved from the clinical trial information database—210—and information indicative of the patient's eligibility or ineligibility to a trial is provided to the user's client computer—212.

If the information indicative of the patient's eligibility or ineligibility to a trial is indicative of the patient being eligible to a clinical trial, the server computer can retrieve the contact information of the clinical trial's coordinator from the clinical trial information database —214—and provides the contact information to the user's client computer—216, for example, by displaying the same or providing a hyperlink.

The user can be prompted to provide information indicative of patient characteristics that is directly related to the clinical trial criteria of the at least a clinical trial and is absent any personal identifying information to ensure the patient's privacy.

Typically, the clinical trial information is indicative of clinical trial inclusion criteria and clinical trial exclusion criteria with the patient being determined to be ineligible to the trial if the patient characteristics: do not meet all inclusion criteria of the respective trial; and do meet one or more exclusion criteria of the respective trial.

In step 206, all patient characteristics may be collected prior submission to the server computer 102 for comparison, allowing the user to review the entered data prior submission. Alternatively, each patient characteristic is directly submitted to the server computer 102 after selection and compared with the respective clinical trial criterion, enabling, for example, collecting first patient characteristics related to clinical trial exclusion criteria and when the patient characteristics meet one or more exclusion criteria of all available clinical trials, the user is presented with a message indicating that there is no clinical trial available for the patient and the process is stopped, thus saving time. Furthermore, the process of collecting patient characteristics may be narrowed to clinical trials for which the patient characteristics do not meet an exclusion criterion.

Figure 7:
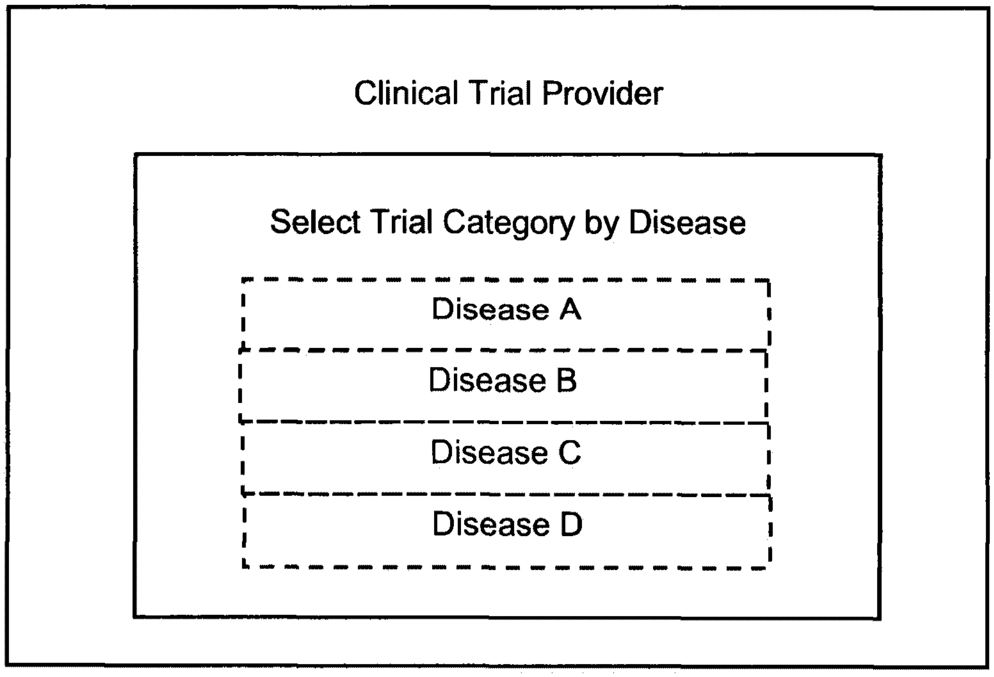
FIG. 7 is a simplified block diagram illustrating a webpage for providing clinical trial information of the method for facilitating clinical trial enrollment according to an embodiment.
Figure 8:
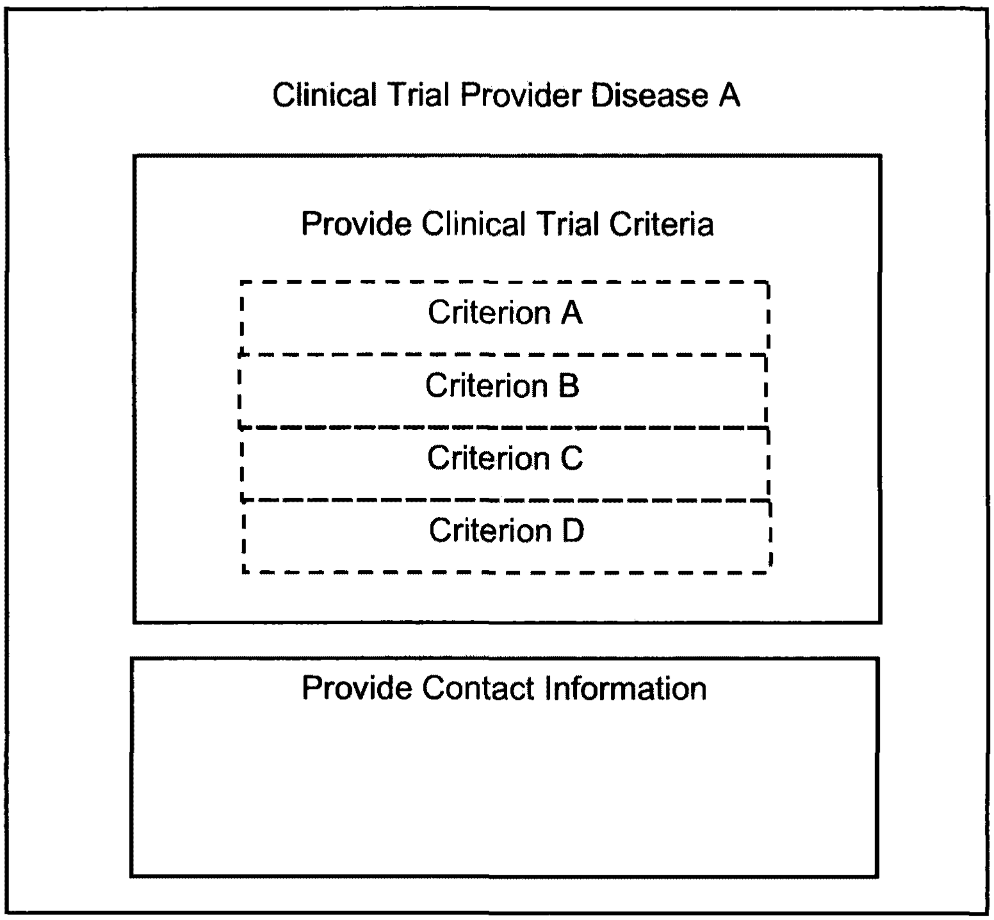
FIG. 8 is a simplified block diagram illustrating a webpage for providing clinical trial information of the method for facilitating clinical trial enrollment according to an embodiment.

As illustrated in FIG. 3, the interactive Internet website can enable communication—302—between the server computer 102 and a client computer of a clinical trial provider connected to the Internet 10. The clinical trial provider is presented with the homepage, an example, of which is illustrated in FIG. 4, enabling to select "Clinical Trial Provider" for providing clinical trial information of a clinical trial, by clicking on the respective button which generates a request for providing clinical trial information—304—at the server computer 102. The clinical trial provider is then prompted and enabled to provide clinical trial information indicative of clinical trial criteria and contact information of the clinical trial's coordinator—306. For example, the clinical trial provider is first presented with a webpage, as illustrated in FIG. 7, enabling to select a disease for which it is desired to provide clinical trial information by using a drop-down menu and clicking on the respective disease such as, for example, disease B "Inflammatory Bowel Disease". Upon selection of the disease, the user is presented with a second webpage, as illustrated in FIG. 6, enabling to provide clinical trial information indicative of clinical trial criteria by using a drop-down menu and contact information in the respective field. Upon receipt of the clinical trial information—308—the same is stored in the clinical trial information database—310.

Alternatively, the clinical trial information may be provided to the server computer 102 by a system administrator, or by the server computer accessing a clinical trial providers database using, for example, hyperlink technology, or a combination thereof.

The present invention has been described herein with regard to preferred embodiments. However, it will be obvious to persons skilled in the art that a number of variations and modifications can be made without departing from the scope of the invention as described herein.

What is claimed is:

1. A method for facilitating clinical trial enrollment comprising:

providing a clinical trial information database, the clinical trial information database having stored therein clinical trial information of at least a clinical trial with the clinical trial information being indicative of clinical trial criteria of the at least a clinical trial and contact information of the at least a clinical trial's coordinator;

providing a server computer connected to the Internet and the clinical trial database, the server computer comprising a database management module, an Internet communication module, a comparison module, and an account management module, each module being associated with the processing of a specific task;

the server computer executing computer-executable instructions stored in a non-transient memory thereof and performing:

generating data indicative of an interactive Internet website for facilitating clinical trial enrollment, the interactive Internet website enabling communication between the server computer and users of client computers connected to the Internet;

receiving from a user, via the Internet website executed on the user's client computer, a request for clinical trial information;

prompting and enabling the user to provide information indicative of patient characteristics that is directly related to the clinical trial criteria of the at least a clinical trial and is absent any personal identifying information, wherein each patient characteristic is directly submitted to the server computer after selection and compared with the respective clinical trial criterion by the comparison module, enabling collecting first patient characteristics related to clinical trial exclusion criteria;

when the patient characteristics meet one or more exclusion criteria of all available clinical trials, presenting the user with a message indicating that there is no clinical trial available for the patient when the patient characteristics meet one or more exclusion criteria of all available clinical trials;

comparing the received patient characteristics with the clinical trial criteria retrieved from the clinical trial information database and providing to the user's client computer information indicative of the patient's eligibility or ineligibility to a trial; and, if the information indicative of the patient's eligibility or ineligibility to a trial is indicative of the patient being eligible to a clinical trial:

the server computer retrieving the contact information of the clinical trial's coordinator from the clinical trial information database; and, the server computer providing the contact information to the user's client computer.

2. The method according to claim 1 wherein the clinical trial information is indicative of clinical trial inclusion criteria and wherein the patient is determined to be ineligible to the trial if the patient characteristics do not meet all inclusion criteria of the respective trial.

3. The method according to claim 1 wherein the clinical trial information is indicative of clinical trial exclusion criteria and wherein the patient is determined to be ineligible to the trial if the patient characteristics do meet one or more exclusion criteria of the respective trial.

4. The method according to claim 1 wherein the clinical trial information is indicative of clinical trial inclusion criteria and clinical trial exclusion criteria, and wherein the patient is determined to be ineligible to the trial if the patient characteristics do not meet all inclusion criteria of the respective trial, and wherein the patient is determined to be ineligible to the trial if the patient characteristics do meet one or more exclusion criteria of the respective trial.

5. The method according to claim 1 wherein prompting and enabling the user to provide information indicative of patient characteristics comprises:

the interactive Internet website displaying characteristics using at least a drop-down menu; and, the user selecting the patient characteristics from the at least a drop-down menu.

6. The method according to claim 1 wherein the user is prompted to provide information indicative of patient characteristics that is directly related to the clinical trial criteria of the at least a clinical trial.

7. The method according to claim 1 wherein the information indicative of patient characteristics is provided absent personal identifying information.

8. The method according to claim 1 wherein the contact information provided to the user's client computer comprises a hyperlink.

9. The method according to claim 1 wherein the server computer further performs:

receiving clinical trial information of a clinical trial with the clinical trial information being indicative of clinical trial criteria of the clinical trial and contact information of the clinical trial's coordinator; and, storing the clinical trial information in the clinical trial information database.

10. The method according to claim 9 wherein the server computer further performs:

enabling via the interactive Internet website communication between the server computer and a client computer of a clinical trial provider connected to the Internet;

receiving from the clinical trial provider, via the Internet website executed on the clinical trial provider's client computer, a request for providing clinical trial information; and, prompting and enabling the clinical trial provider to provide the clinical trial information.

11. The method according to claim 10 wherein prompting and enabling the user to provide information indicative of patient characteristics comprises:

presenting the user with a first webpage, the first webpage enabling the user to select a disease for which it is desired to find a clinical trial; and, upon the selection of the disease, presenting the user with a second webpage, the second webpage enabling the user to provide patient characteristics.

12. The method according to claim 11 wherein the user is enabled:

to select the disease by using a drop-down menu and clicking on the respective disease; and, to provide the patient characteristics by using a drop-down menu and clicking on the respective patient characteristics.

13. The method according to claim 1 further comprising narrowing collecting patient characteristics to clinical trials for which the patient characteristics do not meet an exclusion criterion.

14. The method according to claim 1 prompting and enabling the clinical trial provider to provide the clinical trial information comprises:

presenting the clinical trial provider with a first webpage, the first webpage enabling the clinical trial provider to select a disease for which it is desired to provide clinical trial information; and, upon the selection of the disease, presenting the clinical trial provider with a second webpage, the second webpage enabling the clinical trial provider to provide clinical trial information indicative of clinical trial criteria.

15. The method according to claim 14 wherein the clinical trial provider is enabled:

to select the disease by using a drop-down menu and clicking on the respective disease; and, to provide the clinical trial information indicative of clinical trial criteria by using a drop-down menu and clicking on the respective patient characteristics.

16. The method according to claim 14 wherein the clinical trial provider is prompted and enabled to provide the contact information of the clinical trial's coordinator.

17. A system for facilitating clinical trial enrollment comprising:

a clinical trial information database, the clinical trial information database having stored therein clinical trial information of at least a clinical trial with the clinical trial information being indicative of clinical trial criteria of the at least a clinical trial and contact information of the at least a clinical trial's coordinator;

a server computer connected to the Internet and the clinical trial database, the server computer comprising a database management module, an Internet communication module, a comparison module, and an account management module, each module being associated with the processing of a specific task, the server computer when executing computer-executable instructions stored in a non-transient memory thereof performing:

generating data indicative of an interactive Internet website for facilitating clinical trial enrollment, the interactive Internet website enabling communication between the server computer and users of client computers connected to the Internet;

receiving from a user, via the Internet website executed on the user's client computer, a request for clinical trial information;

prompting and enabling the user to provide information indicative of patient characteristics that is directly related to the clinical trial criteria of the at least a clinical trial and is absent any personal identifying information, wherein each patient characteristic is directly submitted to the server computer after selection and compared with the respective clinical trial criterion by the comparison module, enabling collecting first patient characteristics related to clinical trial exclusion criteria;

when the patient characteristics meet one or more exclusion criteria of all available clinical trials, presenting the user with a message indicating that there is no clinical trial available for the patient when the patient characteristics meet one or more exclusion criteria of all available clinical trials;

comparing the received patient characteristics with clinical trial criteria retrieved from the clinical trial information database and providing to the user's client computer information indicative of the patient's eligibility to a trial; and, if the information indicative of the patient's eligibility or ineligibility to a trial is indicative of the patient being eligible to a clinical trial:

the server computer retrieving the contact information of the clinical trial's coordinator from the clinical trial information database; and, the server computer providing the contact information to the user's client computer.

* * * * *